United States Patent [19]

Becker et al.

[11] Patent Number: 4,795,818

[45] Date of Patent: Jan. 3, 1989

[54] OPTIMIZING THE YIELD OF MALEIC ANHYDRIDE CATALYST

[75] Inventors: Mitchell Becker, Teaneck; John Walden, Hightstown, both of N.J.

[73] Assignee: Scientific Design Company, Inc., Little Ferry, N.J.

[21] Appl. No.: 183,372

[22] Filed: Apr. 11, 1988

Related U.S. Application Data

[63] Continuation of Ser. No. 647,302, Sep. 4, 1984, abandoned.

[51] Int. Cl.$^4$ .............................................. C07D 307/60
[52] U.S. Cl. .................................... 549/260; 549/259
[58] Field of Search ................................ 549/259, 260

[56] References Cited

U.S. PATENT DOCUMENTS

| 2,426,678 | 9/1947 | Greenberg | 502/50 |
|---|---|---|---|
| 3,296,282 | 1/1967 | Kerr | 549/259 |
| 3,474,041 | 10/1969 | Kerr | 502/20 |
| 4,020,174 | 4/1977 | Partenheimer | 549/259 |
| 4,089,807 | 5/1978 | Partenheimer | 549/248 |
| 4,094,816 | 6/1978 | Partenheimer | 502/35 |
| 4,123,442 | 10/1978 | Bakshi | 549/259 |
| 4,151,116 | 4/1979 | McDermott | 502/209 |
| 4,411,818 | 10/1983 | Reuter et al. | 502/35 |
| 4,515,899 | 5/1985 | Click et al. | 549/260 |

FOREIGN PATENT DOCUMENTS

| 1071647 | 2/1980 | Canada . |
| 50-10714 | 4/1975 | Japan . |
| 57-19108 | 4/1982 | Japan . |
| 1291354 | 10/1972 | United Kingdom . |
| 1439489 | 6/1976 | United Kingdom . |
| 1512305 | 6/1978 | United Kingdom . |

*Primary Examiner*—Mary C. Lee
*Assistant Examiner*—Bernard I. Dentz
*Attorney, Agent, or Firm*—Kenneth H. Johnson

[57] ABSTRACT

A method of optimizing the yield of a vanadium-phosphorus catalyst during the oxidation of butane to maleic anhydride, which comprises establishing the temperature at which the catalyst provides the desired percentage conversion and yield of maleic anhydride with the established feed composition and then maintaining that temperature by continuously introducing an amount of a suitable phosphorus compound necessary to prevent a decline in selectivity to maleic anhydride without significantly increasing the temperature.

2 Claims, No Drawings

OPTIMIZING THE YIELD OF MALEIC ANHYDRIDE CATALYST

This application is a continuation of application Ser. No. 647,302, filed Sept. 4, 1984, now abandoned.

PRIOR ART

This invention relates generally to the preparation of maleic anhydride by catalytic oxidation of hydrocarbons, particularly butane. More specifically, the invention relates to a technique for optimizing the yield of the catalyst during use.

Rapid decline in the maleic anhydride yield of vanadium-phosphorus-based catalysts has made commercialization of the butane oxidation process difficult. The reduction in maleic anhydride yield means that more of the butane is fully oxidized to carbon oxides and water and that the total production of maleic anhydride declines, increasing the unit cost of the maleic anhydride produced and requiring relatively frequent catalyst replacement. Skilled workers in the art have suggested various methods of countering this loss of catalyst performance, which may reflect uncertainty as to the reasons for this catalyst deterioration. Some have believed that the valence of the vanadium has been changed to such a degree that a treatment is required to return the vanadium valence to its original value. Others have attempted to remove inactive vanadium from the catalyst. Still others have added phosphorus compounds, either to replace phosphorus lost from the catalyst or merely because it had a regenerative effect without regard to any theory of its effect.

In U.S. Pat. No. 4,123,442, sulfur trioxide was employed to raise the valence of the vanadium to between 3.9 and 4.6 and thereby partially to regenerate the catalyst. In U.S. Pat. No. 4,020,174 (also in U.S. Pat. Nos. 4,089,807 and 4,094,816) halogens or organic halides were disclosed as being useful to reactivate the vanadium-phosphorus catalyst. Removal of the vanadium from the catalyst was found to result from this treatment (see the '807 patent). Some have regenerated the catalyst outside the reactor, as represented by British patent No. 1,439,489, which discloses treatment with a reducing gas such as hydrogen, carbon monoxide, and others. In British patent No. 1,512,305, the catalyst was reclaimed by contact with aqueous ammonia or amines.

A number of patents have discussed the addition of volatile phosphorus compounds to regenerate vanadium-phosphorus catalysts. Sometimes the compounds were added to catalysts containing no phosphorus at all. Usually, this has been done to regenerate the catalysts following a period of declining activity. In U.S. Pat. No. 2,426,678, phosphate catalysts used for dehydration were shown to be regenerated by application of esters of phosphoric acid. In U.S. Pat. Nos. 3,296,282 and 3,474,041, vanadium-phosphorus catalysts used for oxidation of olefins to maleic anhydride were regenerated by adding other types of organic phosphorus compounds, particularly phosphites. In Canadian patent No. 1,071,647, regeneration of butane to maleic anhydride catalysts through the use of the alkyl esters of phosphoric acid was disclosed. In Japanese Kokai No. 75/10,714, maleic anhydride catalysts used for the oxidation of unsaturated hydrocarbons were regenerated to replace phosphorus lost during use by treating with a phosphorus compound in an organic solvent. More recently, in Japanese Kokai No. 82/19,108, tungsten-phosphorus catalysts were maintained by addition of phosphoric acid or derivatives. Addition of tri-isobutyl phosphate to a mixed $C_4$ feed over a titanium-vanadium-phosphorus catalyst was disclosed in British patent No. 1,291,354. In a reated disclosure, U.S. Pat. No. 4,411,818, phthalic anhydride catalysts, principally comprising vanadium and titanium, were reactivated with the addition of volatile phosphorus compounds.

The general disclosures discussed above have been insufficient to permit stable operation of maleic anhydride catalysts so that the yield could be optimized. It has been found that these vanadium-phosphorus catalysts deactivate too rapidly in commercial use, making it difficult to obtain the inherent advantages of employing butane as a feedstock. Attempts to regenerate such catalysts by periodic addition of additives have given mixed results. On the other hand, merely adding phosphorus compounds continuously is not sufficient. If the amount added is too small, continuous loss in maleic anhydride yield occurs; and yet if too much is used, catalyst activity will be lost.

Tests appear to indicate that phosphorus loss occurs at a relatively low level, and this is presumed to be associated with the loss of catalyst performance. Whether addition of phosphorus compounds replaces lost phosphorus or has some other function is unknown. There has been a need to develop a technique for avoiding loss in catalyst activity which is reliable and applicable to the various conditions under which the catalysts may operate. The present inventors have discovered a solution to this problem.

SUMMARY OF THE INVENTION

The process of the invention optimizes the performance of a vanadium-phosphorus catalyst during the oxidation of butane to maleic anhydride. The catalyst operating temperature which provides the desired percentage conversion of butane to maleic anhydride is determined, preferably as soon as possible after the catalyst reaches the design operating conditions. The desired conversion is chosen to achieve the desired optimum yield of maleic anhydride. Then the catalyst operating temperature, or an indirect indicator of such temperature, is monitored to measure the catalyst performance. Changes in the intrinsic catalyst performance result in selectivity loss and are usually indicated by a decline in the temperature necessary to achieve the desired conversion. The temperature decline can be prevented by continuously passing over the catalyst a sufficient amount of a suitable phosphorus compound. The yield of maleic anhydride is maintained. As the catalyst ages, and the selectivity decreases, further increases in phosphorus addition may be needed to maintain the selectivity. In such circumstances the operating temperature is raised, but only as necessary to obtain the desired percentage conversion of butane.

The catalyst operating temperature may be taken as indicated by the outlet gas temperature. One useful indirect indicator is the temperature of the heat removal means, which usually is adjusted to compensate for changes in conversion of maleic anhydride resulting from changes in intrinsic catalyst performance. Where the catalyst is disposed inside the tubes of a shell and tube reactor and surrounded by a circulating heat transfer fluid on the shell side, the exit or inlet temperature of the heat transfer fluid may be used to monitor catalyst performance.

Various phosphorus compounds may be used, including phosphoric acids, phosphates, phosphites, and the like. Most useful are volatile organic phosphorus compounds such as the alkyl phosphates, perferably trimethyl and triethyl phosphate. The amount added will depend upon the catalyst, its history, and the operating conditions and will be found generally in the range of 0.1 to 6 mg P/hr-kg catalyst.

The butane oxidation process typically is carried out at temperatures in the range of 340°–450° C., pressures in the range of 1–5 bar, and gas hourly space velocities in the range 500–5000 $hr^{-1}$. Suitable catalysts are comprised of vanadium-phosphorus in atomic ratios of P/V=0.9–1.8/1 and having a vanadium valence of 3.9–4.5. Preferably, the catalysts will be of the type disclosed in U.S. Pat. No. 4,151,116.

DESCRIPTION OF THE PREFERRED EMBODIMENTS

Butane may be oxidized to maleic anhydride in several ways. Small amounts of butane can be added to air and the mixture passed once-through over a catalyst under conditions suitable for maleic anhydride formation. Since the lower explosive limit is about 1.8 vol % butane in air, this sets an upper limit on the amount of butane used. The reactor effluent is scrubbed to remove the maleic anhydride formed, and the waste gases are then disposed of. In such an operation more than about 80% of the butane is converted, with a selectivity of more than about 50% to maleic anhydride.

In other techniques, a more complete use of the butane is sought by recycling the unconverted feed. These may be classified by the method by which explosive mixtures of butane in air are avoided. Butane concentrations below the lower explosive limit may be used, but typically, higher concentrations are used since they provide better catalyst productivity. If a large amount of butane is used, then the mixture can be above the upper explosive limit at reactor conditions, depending upon the amount of oxygen present. Alternatively, if the oxygen content of the feed mixture is kept below about 13 vol %, any amount of butane may be used, although the low oxygen content limits the amount of butane which can be converted in each pass. These methods may be characterized as using "butane-rich" mixtures. Usually, a smaller fraction of the butane is oxidized in each pass compared to once-through operation, but by recycling concentrated butane a higher overall yield of maleic anhydride is obtained. These methods as well as the conventional "butane-lean" operation have been found to be susceptible to the yield optimization techniques of the invention.

The butane oxidation process is carried out at conditions typical of the art. Depending upon the concentration of butane and oxygen, the intrinsic catalyst performance, and the desired yield of maleic anhydride, the process may be carried out at temperatures in the range of 340°–450° C., pressures in the range of 1–5 bar, and gas hourly space velocities (GHSV) of 500–5000 $hr^{-1}$. Suitable catalysts principally comprise vanadium and phosphorus in atomic ratios of P/V=0.9–1.8/1 and probably will contain promoters in minor amounts, such as are discussed in U.S. Pat. No. 4,151,116. Such catalysts may contain integrally-incorporated promoters plus post-deposited promoters which may be the same or different.

In expressing catalyst performance, the terms "conversion," "selectivity," and "yield" have their conventional meanings. "Conversion" is the percentage of the butane entering the reactor which is converted. "Selectivity" is the percentage of the butane converted which becomes maleic anhydride. "Yield" is the percentage of the butane feed which becomes maleic anhydride.

The oxidation of butane to maleic anhydride produces heat which must be removed. The undesirable oxidation of butane to carbon oxides and water also releases heat. Consequently, the catalyst must be cooled, usually by a circulating stream of a molten salt or other suitable heat transfer fluid. The incoming feed gases are heated to a temperature from which the reaction can begin, and thereafter the temperature of the gases and the catalyst is determined by a balance between the heat of reaction and the heat removed by the circulating heat transfer fluid. The result is a rising temperature to a maximum (the so-called "hot spot") followed by a decline in temperature as the heat removed exceeds the heat released. Thus, the catalyst operating temperature is not a single value, but a "temperature profile" over each of the reactor tubes. It is theoretically possible to measure the "hot spot" or highest catalyst temperature and to use it as an indicator of catalyst performance. However, this is considered impractical since the location and magnitude of the "hot spot" may shift, depending on the operating conditions. Consequently, the temperature of the outlet gases is preferred as the indicator of catalyst operating temperature and inherent catalyst performance. Other indicia are useful, such as the inlet or outlet temperature of the heat transfer fluid.

It has been found that oxidation of butane to maleic anhydride is characterized by an increase in catalyst activity and a loss in selectivity as the catalyst ages, contrary to some rather common reactions where the catalyst loses activity with time and the temperature is raised to maintain the desired activity. With vanadium-phosphorus catalysts the temperature may be reduced to compensate for the increase in catalyst activity. Despite the temperature reduction, the selectivity of the catalyst and the yield of maleic anhydride are lowered. Also, the, equipment design usually establishes a maximum usable temperature, which may limit the operator's ability to adjust process conditions to optimize yield of maleic anhydride.

Typically, these catalysts are operated by establishing the proper operating temperature and then, as the catalyst ages, lowering the temperature to hold the desired conversion of butane. The selectivity of butane conversion to maleic anhydride decreases as well and, consequently, the yield of maleic anhydride falls. Eventually, the catalyst performance has deteriorated so much that it must be replaced. Adjustment of other parameters is not usually convenient in commercial operations but, in principle, changes in feed rates and composition, recycle gas rate (if any), and reactor pressure could be made to offset loss of catalyst yield. Equipment limitations and potential reduction in catalyst life will determine the practical application of such techniques.

The invention will be illustrated and discussed with respect to prior art techniques in the examples below. Broadly, the invention is a new method for controlling the operation of vanadium-phosphorus catalysts to provide the best yield of maleic anhydride from butane. That is, the yield of the catalyst is optimized by continuously introducing a volatile phosphorus compound at a rate established to give maximum yield. Indicative of this condition is the stability of the catalyst operating temperature, or an indirect indicator of such temperature.

Various volatile phosphorus compounds may be used, such as those suggested in the art. It is believed that selection of the phosphorus compound is not critical to the results obtained. More significant are the rate of equivalent phosphorus added and the catalyst performance indicator selected for stabilizing the yield. Particularly useful volatile phosphorus compounds are the alkyl phosphates such as trimethyl and triethyl phosphates. Other classes of phosphorus compounds which may be useful are the organo-phosphorus compounds suggested in U.S. Pat. No. 3,474,041 and phosphoric acid. The amount added will depend upon the catalyst, its history, and the operating conditions and will be found generally within the range of 0.1 to 6 mg P/hr-kg catalyst.

The following examples illustrate the method of the invention and show that methods suggested in the art are insufficient to stabilize the yield of vanadium-phosphorus catalysts.

EXAMPLE 1

A comparison was made of the same catalyst operated with and without continuous addition of a phosphorus compound. Two 915 gm samples of a vanadium-phosphorus catalyst, containing small amounts of titanium and magnesium promoters (nominal formula $V_1$, $P_{2.2}$, $Ti_{0.07}$, $Mg_{0.04}$) and formed into 6.35-mm diameter, 3.18-mm-long cylinders having a 3.18-mm hole in the center, were placed in 3200-mm-long tubes of 25.4-mm O.D. with 2.11-mm wall. The tubes were provided with recirculating salt bath to supply heat to the reactor. (When only a single tube is used, heat losses exceed the heat of reaction, making it necessary to supply heat. In commercial practice, heat must be removed.) The catalysts were brought on stream by operating for a period at low space velocity and normal butane concentration until the desired activity was obtained, after which time the space velocity was gradually raised to achieve the desired test conditions.

In Test A, the operation was continued to maintain a constant butane conversion of about 82% by adjusting the temperature of the circulating salt. (If the catalyst becomes more active, it is necessary to reduce the salt temperature to maintain a constant conversion of butane.) As the test proceeded, the salt temperature was lowered to maintain conversion, and it was found that the yield of maleic anhydride was gradually dropping as catalyst selectivity for maleic anhydride production was lost.

In Test B, trimethyl phosphate (TMP) was continuously added by injecting into the feed gas a 0.79 gm TMP/liter aqueous solution in an amount equivalent to 1.1 mg P/kg cat/hr. Again the salt bath temperature was adjusted to maintain a butane conversion of about 82%. As the test proceeded, the salt temperature was gradually increased; however, the selectivity decline was essentially nil, as shown by the table below, and the yield of maeic anhydride remained steady.

TABLE I

| | Test A (Control) | | Test B (TMP added) | |
| --- | --- | --- | --- | --- |
| % C4 in feed (vol) | 1.5 | | 1.5 | |
| GHSV, hr$^{-1}$ | 2500 | | 2500 | |
| | @ 450 hrs | @ 1750 hrs | @ 830 hrs | @ 1550 hrs |
| Salt temp, °C. | 420 | 407 | 410 | 422 |
| % Conversion C4 | 82 | 82 | 82 | 82 |
| % Selectivity to MAN (mol) | 60 | 52 | 57 | 57 |
| % Yield (wgt) | 82 | 72 | 79 | 79 |
| Yield decline, %/100 hrs | Base | 0.6 | Base | nil |

EXAMPLE 2

The catalyst of Test B was continued in operation for an additional period of about 1,000 hours; no further increase in salt temperature was made, and a decline in yield was observed equal to about 0.7%/100 hours. Therefore, it was concluded that addition of TMP was advantageous, but not capable—at least at the rate used—of arresting catalyst activity decline completely.

EXAMPLE 3

In an experiment similar to that of Example 1, 925 gms of substantially the same catalyst as in Example 1 was loaded into a similar reactor tube and started up in a similar manner. After the break-in period, the conditions of Example 1 (2500 GHSV, 1.5 vol % C4 in air) were used. Instead of adding 1.1 mg P/kg cat/hr, three times as much was added, as a solution of 1.5 gm triethyl phosphate per liter of water. It was found that the yield could be held constant (although no higher than Example 2) but the salt temperature had to be increased at a higher rate than before. It was concluded that more phosphorus was being added than was needed. It did not improve yield, but did lower catalyst activity. The increase in salt temperature was too great (from about 420° C. to 440° C. over a few days' time) to be accepted for a long period of operation, since the maximum design temperature could have been exceeded. This excessive rate of addition offered no yield advantage, but it did lower catalyst activity.

EXAMPLE 4

Part A. In another experiment, about 1,116 gms of catalyst having the same composition as in Examples 1-3 was loaded into a similar reactor and operated as before. An intermediate amount of trimethyl phosphate was added continually, equal to 1.9 mg P/kg cat/hr as a 0.79 gm TMP/liter aqueous solution. It was found that, after an initial rise, the salt temperature remained steady at about 415°-420° C. and required less adjustment to hold 82% conversion of butane, while the yield of maleic anhydride remained relatively steady at about 82% by weight. It was concluded that the amount of trimethyl phosphate being used was the minimum required to achieve maximum yield and therefore was optimum under the operating conditions being used.

As the test proceeded, some further increase of the phosphorus addition rate was made to maintain constant yield, which required that the temperature be increased slightly to about 430° C. Later, another increase in phosphorus addition rate was made, but no significant change in temperature resulted. Selectivity to maleic anhydride was maintained compared to Example 1.

Part B. The catalyst of Part A was operating at a constant yield for 3850 hours. During the next 320 hours, phosphorus addition was discontinued. The catalyst yield dropped about 4 percentage points, equivalent to a rate of about 1.3%/100 hours. The salt temperature had to be lowered from 420° C. to 416° C. to maintain constant conversion. This is a rate normally seen on this catalyst without phosphorus addition. When the phosphorus addition was resumed at the previous rate of about 1.9 mg P/kg cat/hr, the yield and temperature decline stopped almost immediately, and by 5250 hours the maleic anhydride yield had returned to 82% by weight. After 7500 hours, the yield and temperature remained constant.

EXAMPLE 5

(comparative)

In a catalyst test similar to those already described, a "regeneration" was achieved by adding a relatively large amount of phosphorus after the catalyst performance had declined. A 1107 gm charge of a catalyst having a composition similar to that of Example 1, but formed into cylinders having both length and diameter of 4.76 mm, was producing after 1540 hours a 77 wt % yield, having declined from an initial 88.6% yield (1600 GHSV and 1.5% butane in air). Then 850 mg phosphorus per kilogram of catalyst was added as trimethyl phosphate over a 4-5 hour period.

At 1580 hours 340 mg of phosphorus per kg of catalyst was injected over several hours' time. Then, at 1620 hours 260 mg P/kg and again at 1660 hours 170 mg P/kg were added. The effect of these bulk additions of trimethyl phosphate were as follows:

TABLE II

| Operating Hour | Salt Temp. °C. | Weight % Yield of MAN | |
|---|---|---|---|
| | | Before TMP Addition | After TMP Addition |
| 1540 | 414 | 77 | 87 |
| 1580 | 419 | 81 | 85 |
| 1620 | 430 | 79 | 82 |
| 1660 | 433 | 80 | 80 |

As the data show, the improvement in yield obtained by bulk addition of phosphorus was only temporary; the effect decreased so that at 1660 hours no improvement was noted at all. Thus, the "regeneration" technique advocated in the art was found to be inadequate to optimize the yield of maleic anhydride and the operating temperature was becoming excessive.

As the foregoing examples show, selection of an optimum amount of phosphorus is likely to involve carefully controlled tests over a long period of time. It would be expected that the amount required would be affected by the catalyst composition and all of the reaction conditions employed, such as temperature, pressure, and gas composition. Determining the proper amount appeared to be difficult, if not impossible, to predict exactly. In addition, and contrary to the teachings of the art, it had been observed that lost catalyst activity was not fully restored or permanent improvement obtained by adding phosphorus compounds intermittently. Although some improvement could be obtained, restoration of a catalyst to its fresh performance did not seem possible.

It was discovered by the inventors that the empirical selection of a proper amount of phosphorus compound by testing was not effective or reliable. The key to proper maleic anhydride yield optimization was found in selecting an indicator of catalyst condition other than the yield being obtained, since that is the value which is to be managed. This may be the temperature of the reactor effluent which is obtained after the best operating conditions have been established. If this temperature must be lowered to maintain the desired conversion level, the intrinsic catalyst performance is changing and the yield of maleic anhydride will be reduced. However, according to the invention, a phosphorus compound is continuously introduced at a minimum rate selected to maintain maximum catalyst yield while holding the operating temperature constant. The heat transfer medium temperature should only be changed when required to offset changes in catalyst activity resulting from reoptimizing phosphorus addition as the catalyst ages. If the maximum yield is stabilized by this amount of phosphorus addition, then no further change is necessary. If, however, a declining yield is still observed, the level of phosphorus addition should be increased until the appropriate level of phosphorus addition is achieved with little or no increase in operating temperature.

It has been found that the response of the catalyst to phosphorus addition is not as prompt and predictable as would be desired. This appears to be particularly true when small amounts of phosphorus are added. Consequently, a preferred mode of operation is to add continuously the selected phosphorus compound in gradually increasing amounts until an effect on activity is noted which requires a small compensating increase in temperature. This amount of phosphorus provides control of the catalyst performance, but not so much as to cause a significant increase in operating temperature. In this way, the catalyst may be kept at the most productive level without suffering significant yield loss for an extended period of time. As suggested in Example 4, if the catalyst shows a performance decline after a lengthy period, it may be appropriate to increase the phosphorus addition rate to maintain selectivity of butane conversion to maleic anhydride and then to increase the temperature a small amount to compensate for the loss of catalyst activity.

While the most direct measure of catalyst condition would appear to be the effluent gas temperature, it is within the scope of the invention to use instead other, more indirect, measures of catalyst condition. One such measure is is the heat transfer medium temperature itself. In traditional operating technique, the heat transfer medium temperature is adjusted to maintain the conversion of butane, while the yield of maleic anhydride reflects the catalyst performance. Using the new method, the heat transfer medium temperature should be viewed as an indicator of the catalyst condition, and adjustment of the phosphorus injection rate should be made to avoid a change in heat transfer medium temperature if possible. By operating in such a manner, the catalyst is maintained at the same performance level for a longer period than traditionally possible, and the useful catalyst life is significantly extended.

The general usefulness of the operating method discovered by the inventors is shown by the following example in which stable catalyst performance is obtained even though the operating conditions differ significantly from those in the earlier examples.

EXAMPLE 6

In a test simulating conditions typical of a butane-rich recycle operation, 983 grams of a catalyst similar to that of Example 1 was operating at 3500 GHSV with a feed gas containing 2.4 vol % butane, 10 vol % oxygen, balance nitrogen. At a temperature of 370° C. (heat transfer salt) and 4.5 bar, 25% of the butane was converted in a single pass with a 72% selectivity to maleic anhydride. The catalyst showed a performance decline (without addition of phosphorus) of about 1-2% selectivity for each 100 hours of operation. Addition of 0.3 mg P/kg catalyst per hour was begun and found sufficient to halt the catalyst activity decline.

EXAMPLE 7

In another test simulating recycle operation with a butane-rich feed, a 997 gm charge of a catalyst similar to that of Example 1 was tested at 2650 GHSV with a feed gas containing 5.5 vol % butane, 12 vol % oxygen, and balance nitrogen. At 396° C (salt temperature) and 3.4 bar, the conversion of butane was 25% with a 65% selectivity to maleic anhydride. Continuous phosphorus addition was begun at a rate of 0.3 mg P/kg/hr and gradually increased, reaching 0.47 mg P/kg/hr at 600 hours. At that time no yield decline had been observed and the salt temperature remained constant, indicating that the optimum amount of phosphorus was being used.

What is claimed is:

1. In the process for the gas phase partial oxidation of butane for the production of maleic anhydride in the presence of a vanadium/phosphorus catalyst at temperatures in the range of 340° to 450° C., pressures in the range of 1 to 5 bars, and gas hourly sace velocities in the range of 500 to 5000 $hr^{-1}$, said catalyst having an initial atomic ratio of P/V in the range of 0.9 to 1.8/1 and vanadium having an initial valence of 3.9 to 4.5, wherein the improvement comprises operating the process in the absence of added volatile phosphorus compound at a preselected conversion which gives a specific yield of maleic anhydride, determining the temperature of said reaction at said conversion and yield and thereafter maintaining said temperature substantially constant by the controlled continuous addition of a volatile phosphorus compound to said process, whereby the yield of maleic anhydride is maintained substantially constant.

2. The process of claim 1 further comprising the step of compensating for catalyst aging by increasing the amount of said phosphorus compound as required to maintain selectivity, and thereafter increasing operating temperature only as required to provide the desired percentage conversion of butane to maleic anhydride.

* * * * *